United States Patent
Lundquist

(10) Patent No.: US 9,588,123 B2
(45) Date of Patent: Mar. 7, 2017

(54) COMPOSITIONS AND METHODS FOR IN VITRO DIAGNOSTIC TESTS INCLUDING ZWITTERIONIC SOLUBILIZATION REAGENT

(71) Applicant: SurModics IVD, Inc., Eden Prairie, MN (US)

(72) Inventor: Sean Lundquist, Chaska, MN (US)

(73) Assignee: SURMODICS IVD, INC., Eden Prairie, MN (US)

( * ) Notice: Subject to any disclaimer, the term of this patent is extended or adjusted under 35 U.S.C. 154(b) by 0 days.

(21) Appl. No.: 14/683,693

(22) Filed: Apr. 10, 2015

(65) Prior Publication Data

US 2015/0293110 A1    Oct. 15, 2015

Related U.S. Application Data

(60) Provisional application No. 61/978,331, filed on Apr. 11, 2014.

(51) Int. Cl.
| | |
|---|---|
| *G01N 33/58* | (2006.01) |
| *C12Q 1/26* | (2006.01) |
| *C12Q 1/28* | (2006.01) |

(52) U.S. Cl.
CPC .......... *G01N 33/583* (2013.01); *C12Q 1/26* (2013.01); *C12Q 1/28* (2013.01); *G01N 33/581* (2013.01); *C12Q 2326/10* (2013.01)

(58) Field of Classification Search
CPC ..................... A61K 2300/00; G01N 33/583
See application file for complete search history.

(56) References Cited

U.S. PATENT DOCUMENTS

| 4,778,757 A | 10/1988 | Teshima et al. |
| 2004/0219620 A1 | 11/2004 | Mayer |

FOREIGN PATENT DOCUMENTS

| EP | 1 213 358 | 6/2002 | |
| JP | 2012-100654 | 5/2012 | |
| WO | WO-2011121305 A2 * | 10/2011 | ............... A61K 9/08 |

OTHER PUBLICATIONS

Volpe et al., "3,3',5,5'-Tetramethylbenzidine as electrochemical substrate for horseradish peroxidase based enzyme immunoassays. A comparative study," published Jun. 1998.*
Ryan et al., "Thermostabilized chemical derivatives of horseradish peroxidase," published Jun. 1994.*

Al-Okab, R.A., et al., (2008) *New electrophilic coupling reagents for spectrophotometric determination of residual chlorine in drinking water and environmental samples in micellar medium of cetylpyridinium chloride*, Journal of Molecular Liquids 137: 110-115.

Andrews, P.C., and Krinsky, N.I. (1982) *Quantitative determination of myeloperoxidase using tetramethylbenzidine as substrate*. Anal Biochem. 127:346-350.

Bos, E.S., et al. (1981) *3,3',5,5'—Tetramethylbenzidine as an Ames test negative chromogen for horse-radish peroxidase in enzyme-immunoassay*. J. Immunoassay. 2:187-204.

Frey, A., et al. (2000) *A stable and highly sensitive 3,3',5,5''—tetramethylbenzidine-based substrate reagent for enzyme-linked immunosorbent assays*. J. Immunol Methods 233:47-56.

Holland, V.R., et al. (1974) *A safer substitute for benzidine in the detection of blood*. Tetrahedron 30:3299-3302.

Josephy, P.D., et al. (1982) *The horseradish peroxidase-catalyzed oxidation of 3,5,3',5'—tetramethylbenzidine*. J. Biol. Chem. 257:3669-3675.

Keener, W.K., and Watwood, M.E. (2004) *Chloride analysis using 3,3',5,5''—tetramethylbenzidine and chloroperoxidase*. Anal. Biochem. 334:406-408.

Liem, H.H., et al. (1979) *Quantitative determination of hemoglobin and cytochemical staining for peroxidase using 3,3',5,5'—tetramethylbenzidine dihydrochloride, a safe substitute for benzidine*. Anal. Biochem. 98:388-393.

Morrell, J.I., et al. (1981) *Comparison of horseradish peroxidase visualization methods: quantitative results and further technical specifics*. J. Histochem. Cytochem. 29:903-916.

Ping, Z , et al. (2000) *Enzyme immunoassay using a crossed-beam thermal lens technique*. Microchemical Journal 64:257-262.

Pinkus, J.L., and Goldman, L.S. (1977) *A Benzidine Rearrangement and the Detection of Trace Quantities of Blood*. Journal of Chemical Education 54:380-381.

Volpe, G., et al. (1998) *3,3',5,5'-Tetramethylbenzidine as electrochemical substrate for horseradish peroxidase based enzyme immunoassays. A comparative study*. Analyst, Jun. 123:1303-1307.

\* cited by examiner

*Primary Examiner* — Shafiqul Haq
*Assistant Examiner* — Nam Nguyen
(74) *Attorney, Agent, or Firm* — Kagan Binder, PLLC

(57) ABSTRACT

The disclosure is directed to compositions, kits, and methods for performing colorimetric analysis. A composition for a colorimetric assay can be prepared that includes an aromatic amine chromogenic substrate and a zwitterionic solubilization reagent that is N,N,N-trimethylglycine (betaine). The zwitterionic solubilization reagent is highly useful as a non-encapsulating solubilization reagent and provided faster kinetics and increased dye content of an aromatic amine chromogenic substrate in an enzymatic reaction. In turn, this can result in improvements in detection of an analyte in a sample and also can increase the sample throughput. The aromatic amine chromogenic substrate and N,N,N-trimethylglycine solubilization reagent can be used in assays such as ELISAs in order to provide a more accurate and faster detection of analytes in a biological sample.

6 Claims, No Drawings

COMPOSITIONS AND METHODS FOR IN VITRO DIAGNOSTIC TESTS INCLUDING ZWITTERIONIC SOLUBILIZATION REAGENT

The present non-provisional Application claims the benefit of commonly owned provisional Application having Ser. No. 61/978,331, filed on Apr. 11, 2014, entitled COMPOSITIONS AND METHODS FOR IN VITRO DIAGNOSTIC TESTS INCLUDING ZWITTERIONIC SOLUBILIZATION REAGENTS, which Application is incorporated herein by reference in its entirety.

FIELD

The disclosure is directed to compositions and methods for in vitro diagnostic and in vitro colorimetric tests.

BACKGROUND

Research and diagnostic procedures benefit from rapid, accurate, and qualitative and/or quantitative determinations of substances ("analytes") that are present in biological samples, such as biological tissues or fluids, at low concentrations. For example, the presence of drugs, narcotics, hormones, steroids, polypeptides, prostaglandins or infectious organisms in blood, urine, saliva, dental plaque, gingival crevicular fluid, or other biological specimens is desirably determined in an accurate and rapid fashion for suitable diagnosis or treatment.

In many cases, an analyte is identified in a sample using a compound that specifically recognizes the chemical features of the analyte. Often, monoclonal antibodies specific for one or more chemical epitopes on an analyte are used. In other cases, oligonucleotides that are specific for gene transcripts (e.g., mRNA analytes) can be used to assess gene expression in a cell-containing sample.

The complex formed between the antibody (or oligonucleotide) and analyte can be detected by a variety of known methods. The most commonly used methods employ a signal generating moiety of some type which is either already attached to the antibody/oligonucleotide, or becomes attached to the antibody/oligonucleotide through further reaction. For example, in the formation of a complex of biotin with avidin, the complex may be detected using a label on either the avidin or biotin molecule. Such a label may be a radioisotope or an enzyme conjugated to the avidin or biotin. Alternatively, the avidin-biotin complex might be detected by further reaction with a labeled molecule which is specific to either or both parts of the complex. It is commonly known to do the same with antigens and their corresponding antibodies.

During an analysis procedure, the specific binding ligand of interest (such as an antigen from an infectious agent) is often detected using colorimetric, fluorescent, or chemiluminescent signals resulting from reaction of the enzyme label with its corresponding substrate.

In many colorimetric assays, a sample containing analyte is mixed with detection reagents and a colored product is produced if the analyte is present. Analysis can be carried out for a predetermined time after the assay is started (end point analysis), or can be performed over time to assess the generation of color (kinetic analysis). Both types of assays are directed at determining the amount of analyte in the sample. For endpoint analysis, the intensity of the colored reaction (e.g., as measured by the absorbance value of the colorimetric reaction product) is directly proportional to the amount of analyte present. Here, the presence of a large amount of analyte can result in a more intense color. For kinetic analysis, the time required before the appearance of a color (reaction time) is inversely proportional to the amount of analyte present. Here, the presence of a large amount of analyte can result in a rapid reaction. The concentration of analyte in test samples can be calculated from a standard curve.

Some problems associated with colorimetric analysis are that colorimetric reagents can have chemical properties causing them to exhibit poor solubility in assay compositions. Excipient components intended to improve solubility characteristics can potentially interfere with one or more aspects of the assay. Such interference can yield results that do not accurately reflect the amount of analyte in the sample or can significantly slow the reaction time.

SUMMARY

Generally, the disclosure is directed to compositions, kits, and methods for determination of an analyte in a sample which use an aromatic amine chromogenic substrate and a zwitterionic solubilization reagent for the chromogenic substrate that is N,N,N-trimethylglycine (betaine). Experimental studies associated with the disclosure found that N,N,N-trimethylglycine is highly useful as a non-encapsulating solubilization reagent and provided faster kinetics and increased dye content of an aromatic amine chromogenic substrate in an enzymatic reaction. The N,N,N-trimethylglycine provides an advantage over encapsulating reagents that, despite improving chromogenic substrate solubility, can slow down kinetic activity.

Accordingly, one aspect of the disclosure is directed to a kit with components for performing a colorimetric assay. The kit comprises an aromatic amine chromogenic substrate, such as a benzidine chromogenic substrate like 3,3',5,5'-tetramethylbenzidine (TMB), and a zwitterionic solubilization reagent that is N,N,N-trimethylglycine.

In the kit, the aromatic amine chromogenic substrate and the N,N,N-trimethylglycine can be separate or in mixture. The aromatic amine chromogenic substrate is capable of forming a chromogenic reaction product detectable using colorimetric analysis in a method using the kit components. The kit can optionally include other components like one or more redox compounds, such as peroxidases, peroxidase substrates, oxidases, and oxidase substrates, which can be used to convert the chromogenic substrate into the chromogenic reaction product. Another optional kit component is an analyte binding member, such as an antibody, capable of specific recognition of an analyte of interest in a biological sample. Other optional components in the kit include vessels, such as multiwell plates, in which the colorimetric analysis can be carried out and the chromogenic reaction product read using spectrophotometric equipment. The kit can also include instructions for carrying out the colorimetric assay.

In other embodiments, the disclosure is directed to a composition comprising the zwitterionic solubilization reagent that is N,N,N-trimethylglycine and an aromatic amine chromogenic substrate used for colorimetric analysis. In some aspects the composition may be referred to as a "pre-reaction composition" if the chromogenic substrate is not yet converted to its reaction product. The composition can optionally include other components useful for generating the chromogenic reaction product, such as an analyte binding member or an enzyme. The disclosure also provides a composition formed following enzymatic reaction (i.e., "a post-reaction composition") comprising an enzyme, an aromatic amine chromogenic reaction product, and a zwitterionic solubilization reagent that is N,N,N-trimethylglycine. The (post-reaction) composition can optionally include other components useful detection of the benzidine chromogenic reaction product, enzyme, such as an analyte binding member or an enzyme.

In other embodiments, the disclosure is directed to methods for performing a colorimetric analysis. The method includes steps of: (a) providing a reaction composition comprising a zwitterionic solubilization reagent that is N,N,N-trimethylglycine, an enzyme, and an aromatic amine chromogenic substrate; (b) allowing the reaction composition to form an aromatic amine chromogenic reaction product; and, after step (b), (c) performing colorimetric analysis on the composition comprising the chromogenic reaction product. The chromogenic reaction product may be colorimetrically analyzed using equipment such as a spectrophotometer, or alternatively, analyzed by visualization. The method can optionally include one or more steps upstream of the step (a). For example, the method can optionally include one or more steps of providing a biological sample having an analyte, contacting the analyte with an analyte-binding compound, recognizing the analyte/analyte-binding compound complex with one or more components, such as peroxidase, peroxidase substrates, oxidases and oxidase substrates that promote conversion of the chromogenic substrate, and formation of the reaction product detectable using colorimetric analysis.

DETAILED DESCRIPTION

Embodiments of the present disclosure described herein are not intended to be exhaustive or to limiting to the precise forms disclosed in the following detailed description. Rather, the embodiments are chosen and described so that others skilled in the art can appreciate and understand the principles and practices of the present disclosure.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The present disclosure is directed to compositions, kits, and methods for performing a colorimetric assay using an aromatic amine chromogenic substrate and a zwitterionic solubilization reagent that is N,N,N-trimethylglycine. In experiments associated with the disclosure, it was found that N,N,N-trimethylglycine is highly useful as a non-encapsulating solubilization reagent for the chromogenic substrate, and provided faster kinetics and increased dye content of an aromatic amine chromogenic substrate in an enzymatic reaction.

Increasing chromogenic substrate solubility is important in enzymatic reactions as it allows the enzyme to function at maximum velocity, which in turn provides more accurate results. Increasing the rate of the enzymatic reaction is also valuable as it can provide increased throughput for processing samples.

N,N,N-trimethylglycine is a zwitterion (also referred to as an "inner salt"). Zwitterions are a class of molecules having positive (cationic) and negative (anionic) electrical charges (i.e., that has at least two ionic states in the molecule). The positive and negative charges can cancel each other out to provide a neutral molecule.

More specifically, N,N,N-trimethylglycine is a betaine. A "betaine" has a positive (cationic) group having no hydrogen atom (such as quaternary ammonium), and a negative (anionic) group such as a carboxylate group. N,N,N-trimethylglycine is also known as "glycine betaine" and the "original" betaine.

N,N,N-trimethylglycine can, in some cases, be provided in the kit in dried (e.g., lyophilized) form. N,N,N-trimethylglycine can be present in a container, such as a vial. In preparing for use, a solvent can be added to the container to dissolve the N,N,N-trimethylglycine. The solvent can optionally be provided in the kit as well. N,N,N-trimethylglycine can, in other cases, be provided in dissolved form, such as concentrated in a liquid solvent. For example, N,N,N-trimethylglycine is freely soluble in water (up to 64 g/100 mL at 25° C.; ~5.5 M), and therefore N,N,N-trimethylglycine can be provided dissolved in solution in an amount in the range between the working concentration in the colorimetric assay and the maximum solubility limit. For example, in some cases N,N,N-trimethylglycine is supplied in the kit in an aqueous solution with N,N,N-trimethylglycine having a concentration in the range of about 1% w/v to about 50% w/v, or more specifically in the range of 5% w/v to about 25% w/v.

The kits, compositions, and methods of embodiments of the disclosure also include an aromatic amine chromogenic substrate for colorimetric analysis. In an assay, the aromatic amine chromogenic substrate is subjected to a chemical reaction, such as one associated with an enzymatic reaction, resulting in an aromatic amine chromogenic "reaction product" detectable using colorimetric analysis. For example, in an assay, an aromatic amine chromogenic substrate can undergo chemical oxidation or reduction, or chemical modification by the addition, subtraction, or rearrangement of chemical groups on the chromogenic substrate. The aromatic amine reaction product can be one where, for example, the oxidized or reduced form the aromatic amine chromogenic substrate, or a chemical group modified form of the aromatic amine chromogenic substrate, is detectable by colorimetric analysis.

An "aromatic amine chromogenic substrate" is one including an aryl (or aryl ring system) and an amine group, wherein the amine group is bonded to an atom in the aryl ring (or system), and includes the following chemical features:

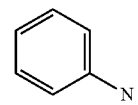

An aryl ring system can include an aryl ring fused to or more other rings, as exemplified by naphthalene, phenalene, anthracene, indacene, indene, including heterocyclic aryl ring systems such as acridine, carbozole, quinoline, indole, indolizine, and benzofuran as well. The one or more aryl rings of the aromatic amine chromogenic substrate can be substituted ("ring substituted") or unsubstituted. The aromatic amine chromogenic substrate can include one or more amine group(s), at least one of which is bonded to the aryl ring.

Aromatic amine chromogenic substrates include "benzidine chromogenic substrates," which refer to compounds selected from benzidine (biphenyl-4,4'-diamine) or having a benzidine core, and ring and/or amine group substituted derivatives thereof. The benzidine chromogenic substrates can form a reaction product usable for colorimetric analysis. In some embodiments, the kits, compositions, and methods of the embodiments of the disclosure use a benzidine derivative such as 3,3',5,5'-tetramethylbenzidine. Benzidine derivatives include those of the following formula:

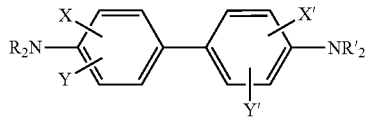

where X, X', Y and Y' and R and R' are independently hydrogen, alkyl, or alkoxy, with the alkyl or alkoxy group(s) having up to six carbon atoms. More specifically, X, X', Y and Y' and R and R' are independently hydrogen, alkyl, or alkoxy, with the alkyl or alkoxy group(s) containing four or less carbon atoms. Benzidine chromogenic substrates include 3,3',5,5'-tetramethylbenzidine, o-tolidine, o-dianisidine, and N,N,N',N', tetramethylbenzidine. See, for example, U.S. Pat. No. 6,376,252.

In the presence of horseradish peroxidase (HRP) and hydrogen peroxide, tetramethylbenzidine (3,3',5,5'-tetramethylbenzidine; TMB) is oxidized to form colored products. As described by Josephy et al. (1982; J. Biol. Chem. 257:3669-3675), TMB ($\lambda_{max}$ 285) is oxidized to form oxidized TMB, a blue product ($\lambda_{max}$ 652) which is a one-electron oxidation product, and then is further oxidized to form a yellow product (X. 450), which is the two-electron oxidation product. Colorimetric analysis and measurement of the reaction product is typically carried out at 450 nm, but can also be observed with the unaided human eye (Reaction Sequence A).

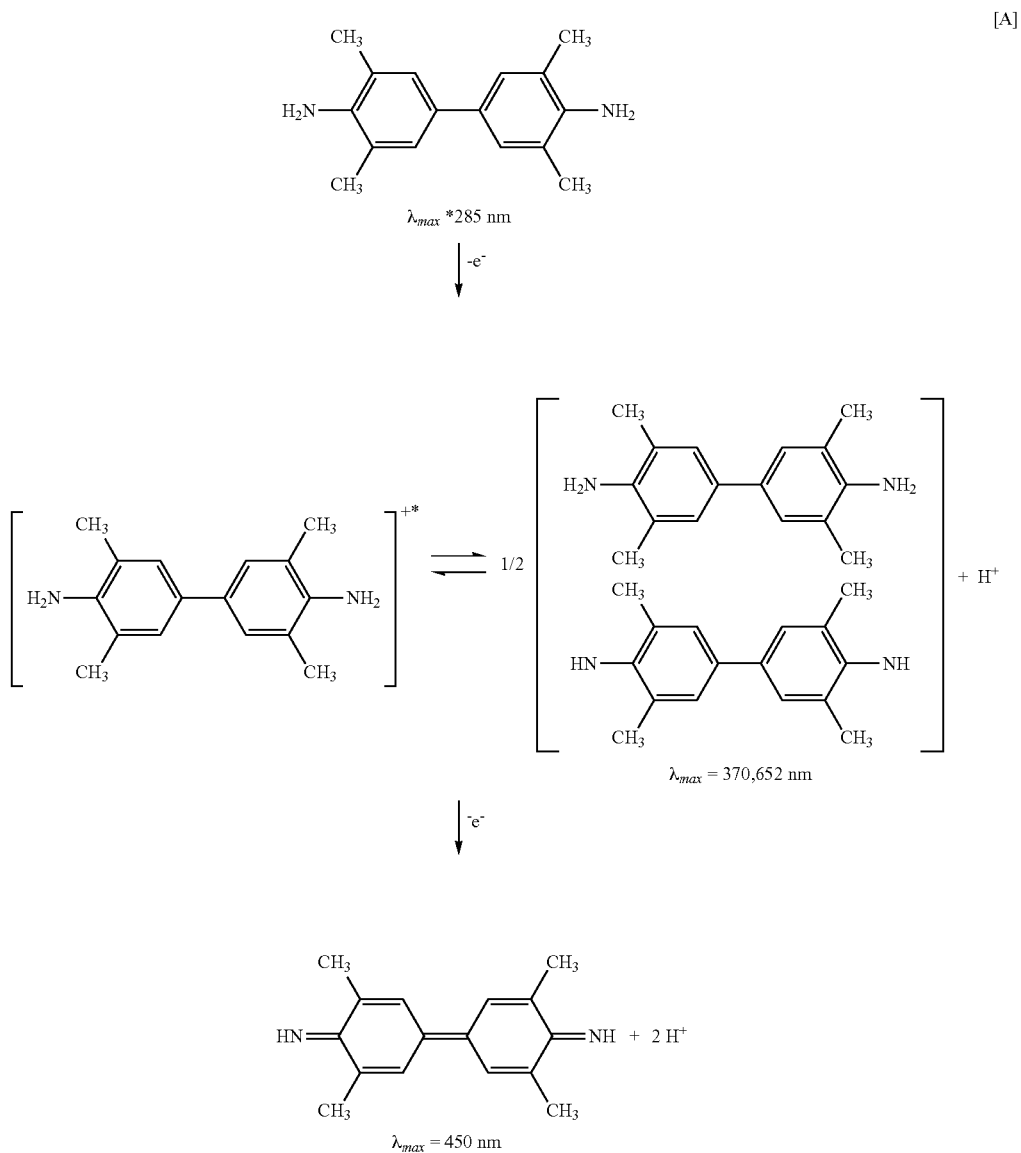

Benzidine chromogenic substrates contemplated for use with the current disclosure include, but are not limited to, benzidine, ortho-tolidine, and ortho-dianisidine, which can change color in the presence of peroxidase-containing components.

Benzidine (in the absence of the N,N,N-trimethylglycine solubilization reagent) is poorly soluble in water (0.94 g/100 mL at 100° C.).

Aromatic amine chromogenic substrates also include phenylpyrazone and derivatives thereof. Phenylpyrazone or a derivative thereof can be used along with phenolic or an aromatic amine compound as chromogenic materials, which are known in the art as Trinder reagents. In the chemistry of peroxidase reactions with Trinder reagents, two colorless organic molecules form a colored product in the presence of peroxidase and hydrogen peroxide.

Exemplary phenylpyrazone derivatives include 4-aminoantipyrine, and exemplary phenols include cresol and salicylamide; other exemplary phenylpyrazone derivatives and phenols are described in U.S. Pat. No. RE29,498. Other exemplary aromatic amines include N,N-dialkylaniline compounds, N,N-dialkyl-m-toluidine compounds, toluidine and aniline sulphopropyl derivatives, N-ethyl-N-(3-sulphopropyl)-m-anisidine, and N-ethyl-N-(2-hydroxyethyl)-m-toluidine, as described in U.S. Pat. No. 5,206,006.

Aromatic amine chromogenic substrates also include phenylenediamine (OPD) and derivatives thereof. OPD is a substrate for horseradish peroxidase (HRP) that produces a yellow-product detectable at 450 nm. Addition of acid to the OPD reaction product produces a yellow-orange with an absorbance maximum of 492.

The N,N,N-trimethylglycine solubilization reagent can be used in combination with any aromatic amine chromogenic substrate. As discussed herein, the N,N,N-trimethylglycine solubilization reagent is particularly useful for improving the solubility of an aromatic amine chromogenic substrate demonstrating poor water solubility, while also increasing the kinetic rate of the chromogenic reaction. However, the N,N,N-trimethylglycine solubilization reagent can also be used in combination with any aromatic amine chromogenic substrate, including those having good water solubility.

For purposes of discussing aspects of the disclosure, reference is made to solubility standards as known in the art. Solubility refers to the level to which a solute dissolves in a solvent. For a chromogenic substrate in a particular solvent, "practically insoluble", or "insoluble" refers to having a solubility of 1 part agent per more than 10,000 parts of solvent, "very slightly soluble" refers to having a solubility of from 1 part agent per 1000 to 10,000 parts of solvent; "slightly soluble" refers to having a solubility of 1 part agent per from 100 to 1000 parts of solvent; "sparingly soluble" refers to having a solubility of 1 part agent from 30 to 100 parts of solvent; "soluble" refers to having a solubility of at least 1 part agent per from 10 to 30 parts solvent, "freely soluble" refers to having a solubility of at least 1 part agent per from 1 to 10 parts solvent, or "very soluble" refers to having a solubility of greater than 1 part agent per from 1 part solvent. These descriptive terms for solubility are standard terms used in the art (see, for example, *Remington: The Science and Practice of Pharmacy*, 20th ed. (2000), Lippincott Williams & Wilkins, Baltimore, Md.).

In some modes of practice, the N,N,N-trimethylglycine solubilization reagent can improve the solubility of an aromatic amine chromogenic substrate that is soluble, or less than soluble, for example, that is sparingly soluble, slightly soluble, very slightly soluble, or practically insoluble. For example, benzidine (in the absence of the N,N,N-trimethylglycine solubilization reagent) is very slightly soluble (also known as "poorly soluble") in water (0.94 g/100 mL at 100° C.), and 2-tolidine is slightly soluble in water (1.3 g/L). In some modes of practice, the solubility of a very slightly soluble chromogenic substrate, such as 3,3',5,5'-tetramethylbenzidine, is enhanced by mixing with a N,N,N-trimethylglycine solubilization reagent. The amounts of N,N,N-trimethylglycine can be determined by one of skill in the art according to factors such as the type of chromogenic substrate used for the assay, the detection reagents used in the assay, the reaction conditions, and the method for analyzing the results of the chromogenic assay.

In exemplary modes of practice, the aromatic amine chromogenic substrate, such as TMB, is present in a composition with the N,N,N-trimethylglycine solubilization reagent in solution having a concentration in the range of about 0.1 M to 5 M, or in the range of 0.25 M to 2 M. The N,N,N-trimethylglycine solubilization reagent may increase the solubility of the chromogenic substrate up to about 100%, up to about 200%, or even up to about 500%. For example, the presence of the N,N,N-trimethylglycine solubilization reagent can increase the solubility of a TMB substrate from about 0.75 mM to about 10 mM or greater.

Therefore, in some arrangements, a kit can be supplied with a reagent composition, such as one where the N,N,N-trimethylglycine solubilization reagent is in dry form (lyophilized), or is present in solution, such as in a concentrated amount (e.g., 5% w/v to about 25% w/v) relative to the working amount of the N,N,N-trimethylglycine solubilization reagent in the chromogenic assay. The kit also includes a chromogenic substrate, which can be in dry form or present in solution, such as a working or concentrated solution.

Prior to carrying out the chromogenic assay, a user can combine the N,N,N-trimethylglycine solubilization reagent and aromatic amine chromogenic substrate at desired concentrations. For example, the working concentration of the N,N,N-trimethylglycine solubilization reagent can be in the range of about 0.1 M to 5 M, or in the range of 0.25 M to 2 M, and the working concentration of the aromatic amine chromogenic substrate can be in the range of about 0.5 µM to about 10 mM, from about 10 µM to about 8 mM, or about 100 µM to about 4 mM.

In other arrangements, a kit can be supplied with the N,N,N-trimethylglycine solubilization reagent and aromatic amine chromogenic substrate in pre-mixed form. For example, the pre-mixture can include the N,N,N-trimethylglycine solubilization reagent and aromatic amine chromogenic substrate in dried form, present in amounts of a desired ratio. A user can add liquid to the dried mixture to provide a working composition, such as with the components present in the working concentrations as described herein. Alternatively, the pre-mixture provide the N,N,N-trimethylglycine solubilization reagent and aromatic amine chromogenic substrate in solution, such as present in the working concentrations as described herein. For example, in some embodiments, the N,N,N-trimethylglycine solubilization reagent (mol) and aromatic amine chromogenic substrate (mol) are present in the composition in a molar ratio in the range of 10:1 to 15,000:1, or more specifically in the range of 20:1 to 1,000:1, respectively.

The kit can also include reagents for the detection of an analyte and colorimetric analysis. For example, the kit can optionally include an analyte specific binding member. The analyte specific binding member can be used for the detection of an analyte of interest in a biological sample. The kit can also optionally include an enzyme for promoting the conversion of the aromatic amine chromogenic substrate to a product. The enzyme can be, for example, a peroxidase, an oxidase, or a conjugate of a peroxidase or an oxidase. The kit can also optionally include an analyte positive control, an analyte negative control, or mixtures thereof. The kit can also optionally include an analysis plate upon which a colorimetric analysis can be performed.

Generally, colorimetric analysis can be performed to determine the presence and/or amount of an analyte in a sample. The term "analyte" refers to any substance or chemical constituent of a sample that is being analyzed. The analyte can be a natural compound, such as one that is produced by an organism, or can be a non-natural compound, such as a synthetic compound used as a bio-affecting agent like a drug, a pesticide, or an herbicide. Methods, compositions and kits of the embodiments of the disclosure can be used for the determination of analytes in numerous industries including, but not limited to health care, food manufacture and processing, chemical analysis and production, agriculture, environmental control, and the like. In some aspects, an ELISA (enzyme-linked immunosorbent assay) is used for detection of an analyte, and the ELISA kit or method uses the N,N,N-trimethylglycine solubilization reagent and aromatic amine chromogenic substrate.

As described herein, a colorimetric analysis or colorimetric assay can be conducted using specialized equipment known in the art to quantify and measure the wavelength and/or absorbance of the solution being analyzed. Such equipment includes, but is not limited to UV-visible spectrophotometers and multiwell plate readers. In some embodiments, the colorimetric analysis or colorimetric assay may be conducted, and endpoint determined, using the unaided human eye. In other embodiments, colorimetric analysis is performed using a kinetic rate assay method, in which the change in absorbance of the reaction solution caused by generation of the aromatic amine chromogenic substrate is monitored over time.

Various types of analytes can be detected and quantified in a sample using the methods of the disclosure. In some aspects, detection of the analyte is facilitated by using an analyte binding member, such as an antibody. In other aspects, methods of the disclosure provide for detection of an analyte without utilizing an analyte binding member. Non-limiting exemplary analytes include drugs, drug metabolites, biomarkers, hormones, antibiotics, food supplements, food additives, naturally occurring contaminants, dyes, microorganisms and their toxins, fungi, viruses, pesticides, herbicides, organic components of waste discharges, tissue specific markers, tissue specific enzymes, cytokines, chemokines, growth factors, receptor ligands, enzymes, nucleic acids, lipids, and small organic molecules, such as glucose and peroxides.

For example, in the food processing and manufacturing industries for humans, as well as domesticated and farm animals, ELISAs are used for the detection of various analytes that are polypeptides, such as soy proteins and gluten, which can be allergens, and other compounds such as antibiotics and hormones.

As other non-limiting examples, in the health care industry ELISAs are used for the detection of various analytes in blood, serum, urine, and other body fluids for the detection of analytes such as erythropoietin (EPO), adrenocorticotropic hormone (ACTH), calcitonin, parathyroid hormone (PTH), thyroid stimulating hormone (TSH), prostate-specific antigen (PSA), human chorionic gonadotropin (HCG), follicle stimulating hormone (FSH), and growth hormone (GH).

The sample including an analyte to be detected can be a biological or a non-biological sample.

A biological sample can be any material taken from an organism such as body fluid from a mammal, material derived from an organism, or a sample that has organisms in it. Biological samples include certain tissues, or body fluid such as blood, sputum, urine, saliva, mucus, vitreal fluid, synovial fluid, semen, cerebrospinal fluid, bone marrow, amniotic fluid, bile, sweat, etc. Biological samples can be obtained from patients and analyzed for the absence or presence of analytes associated with disease states. Quantitation of an analyte can be used to determine the absence, presence or degree of a disease state. Biological samples can also include sections of tissues such as frozen sections taken for histological purposes which can also be analyzed for analytes associated with disease states.

Other biological samples can be those derived from fermentation, cell culturing, bio-fuel production, wastewater treatment, and agriculture. These include food products such as milk, wine, beer, and the like; chemical streams, or waste streams from chemical plants, rivers, and the like. Where the sample is initially complex, solid, or viscous, it may need to be extracted, dissolved or diluted in order to obtain a sample having the appropriate characteristics for use in the immunoassay.

An example of a non-biological sample is a composition of a chemically-synthesized component, such as a synthetic drug for human treatment or a synthetic pesticide for agricultural use.

Analyte detection and the chromogenic assay can be performed in a suitable assay vessel. An assay vessel is any suitable receptacle in which analyte detection, such as by ELISA, and the chromogenic assay can be performed. The assay vessel can be made from material such as glass (e.g., surface modified glass), quartz, or plastic, such as polystyrene, polypropylene, and polycarbonate. Exemplary assay vessels are single and multi-well plates, such as medium and smaller-welled plastic plates such as 6, 24, 96, 384, and 1536 well plates. These are commonly known in the art as microtiter plates, microplates, or microwell plates. Exemplary plates for use in chromogenic assays in each well hold from microliter to milliliter volumes of liquid. Other types of assay vessels that can be used for analysis include capillary tubes. The assay vessel can optionally be included in a kit, or can be supplied by the user to carry out chromogenic assay methods as described herein.

For example, in some modes of practice, 96-well plates are used for analyte detection and the chromogenic assay. A single well in a 96-well plate generally holds up to about 300 µL to 350 µL of liquid, and all or a fraction of this volume can be used during steps in methods of the embodiments of the disclosure. This can provide a convenient volume for steps in ELISA chromogenic assays, involving antibody, analyte, and enzyme immobilizations, dispensing a biological sample, washing steps, dispensing a chromogenic substrate, and the addition of a stop reagent for the colorimetric analysis. The area on the bottom of a 360 µL well is about 0.32 $cm^2$.

In some cases, it is not necessary to identify the analyte (to be detected) in the biological sample with an analyte binding member, such as an antibody. Some assays use enzymes to directly measure biological substances in samples without requiring an antibody-based analyte binding member. For example, some assays use a peroxidase enzyme to measure peroxides present in a sample. Conversely, some assays detect the presence of biological enzymes by using the enzyme's corresponding substrate.

For example, addition of hydrogen peroxide to a sample can be used to test for peroxidase enzymatic activity.

In some modes of practice, the kit, composition, and/or method is used for an enzyme-linked immunosorbent assay (ELISA). Generally, an ELISA uses a solid-phase immunoassay to detect the presence of an analyte in a liquid sample. Various ELISA formats are known in the art, and any of these can be used in conjunction with the N,N,N-trimethylglycine solubilization reagent and aromatic amine chromogenic substrate. Although antibodies are typically used in ELISAs, any sort of analyte-binding member can replace the antibody to provide analyte specific interaction. As such, methods of the disclosure can be used with any enzyme-linked solid phase analyte binding assay. The methods of the disclosure can include any analyte-binding reagent immobilized on the solid phase, along with a detection reagent that will bind specifically and use an enzyme to generate a signal that can be quantified. Embodiments of the disclosure are not limited to any type of analyte binding assay, or any type of analyte binding member, but some examples are discussed to illustrate aspects of embodiments of the disclosure. The particular immunoassay format employed will depend on the particular analyte characteristics, the sample characteristics, the available reagents, and the like.

One example of a common ELISA format is the "direct, antigen down" ELISA which is often used when the biological substance measured is an antibody. In this format a purified protein (the antigen) is absorbed to the plastic surface of a multi-well plate. The plate is washed to remove excess antigen and then blocked with a blocking agent that can be protein based or synthetic, to prevent non-specific binding of the antibody. Next, a sample is added to the well that includes antibodies that specifically bind the antigen immobilized on the plastic surface. Excess sample is then washed off. After washing, secondary antibody conjugated to a peroxidase enzyme specific for the animal antibody in the biological sample is added. For example, if the sample is human, an anti-human antibody (e.g., an anti-human IgG) can be used for detection. A chromogenic reaction can then be performed by adding a reactant, such as hydrogen peroxide, for the peroxidase along with the N,N,N-trimethylglycine solubilization reagent and aromatic amine chromogenic substrate. Optionally, after the reaction proceeds for a desired period of time, a stop reagent can then be added to the chromogenic reaction, and colorimetric analysis can be performed using a spectrophotometer.

In other modes of practice, colorimetric analysis is performed using a kinetic rate assay method, in which the change in absorbance of the reaction solution caused by generation of the aromatic amine chromogenic substrate is monitored over time.

In other cases, for example, a "sandwich" ELISA can be performed by first immobilizing the analyte binding member (e.g., an analyte "capture" antibody) on the solid substrate, such as a plastic well. The plastic surface is then typically blocked with a non-specific protein to prevent adherence of components from the biological sample when added to the well in a next step. Analyte from the biological sample added to the well specifically interacts with the immobilized antibody on the plate. The plate is washed and then a solution of a second analyte binding member (such as an antibody conjugated to a peroxidase enzyme, called a detection antibody) is added which interacts with the analyte already immobilized by the plastic bound antibody. The analyte therefore effectively becomes "sandwiched" between the antibody absorbed on the plate, and the enzyme-conjugated antibody. A chromogenic reaction can then be performed by adding a reactant, such as hydrogen peroxide, for the peroxidase which can be in mixture with the N,N,N-trimethylglycine solubilization reagent and aromatic amine chromogenic substrate. A stop reagent compound can optionally be added, and colorimetric analysis performed; or a kinetic rate assay method is performed.

Alternatively, the "sandwich" approach can be performed by first mixing an enzyme-conjugated antibody with a biological sample having an analyte. The enzyme-conjugated antibody is used in excess and analyte-enzyme-conjugated antibody complex forms in the sample. The sample is then transferred to a well of an assay plate that has the analyte capture antibody immobilized thereon. The analyte capture antibody binds the analyte-enzyme-conjugated antibody complex, and then the well can be washed to remove non-bound material. A chromogenic reaction can then be performed using the N,N,N-trimethylglycine solubilization reagent and aromatic amine chromogenic substrate.

As noted, kits of the disclosure can include one or more components useful for performing an ELISA, other than the N,N,N-trimethylglycine solubilization reagent and aromatic amine chromogenic substrate. The kit can include optional components such as analyte-binding members like antibodies, enzymes (e.g., HRP-linked anti-IgG antibodies, etc), and enzyme substrates. The kit can also include vessels, such as multi-welled plates, in which the chromogenic reaction can take place and be analyzed.

In some aspects, the assay uses a compound having specific affinity for the analyte. A compound with specific affinity is referred to herein as a "binding moiety," which refers to any sort of chemical group that can bind or interact with the analyte. The binding moiety can include naturally occurring molecules or derivatives of naturally occurring molecules, or synthetic molecules, such as small organic molecules, or larger synthetically prepared molecules, such as polymers. Examples of binding moieties include polypeptides, nucleic acids, polysaccharides, and portions of these types of molecules that can bind a target species.

The binding moiety can be an antibody, which is a protein that recognizes a particular epitope on the analyte. In this regard, the analyte may also be referred to as an "antigen" as it is common for antibody-antigen interactions to be described. An antibody can be a polyclonal antibody, a monoclonal antibody or a genetically engineered molecule capable of binding the corresponding member of a specific binding pair. Antibodies as well as antibody fragments can be used for binding to an analyte of interest, and can be included in the methods, kits, and compositions of the disclosure.

Antibody and antibody fragments having specificity towards desired analytes are commercially available or can be prepared by techniques known in the art. For example, monoclonal antibodies (mAbs) can be obtained by any technique that provides for the production of antibody molecules by continuous cell lines in culture. These include, for example, the hybridoma technique (Kohler and Milstein, Nature, 256:495-497 (1975)); the human B-cell hybridoma technique (Kosbor et al., Immunology Today, 4:72 (1983); and the EBV-hybridoma technique (Cole et al., Monoclonal Antibodies and Cancer Therapy, Alan R. Liss, Inc., pp. 77-96 (1985)). Such antibodies may be of any immunoglobulin class including IgG, IgM, IgE, IgA, IgD, or any subclass thereof.

Fab or Fab'2 fragments can be generated from monoclonal antibodies by standard techniques involving papain or pepsin digestion, respectively. Kits for the generation of Fab or Fab'2 fragments are commercially available from, for example, Pierce Chemical (Rockford, Ill.).

In some cases, the binding moiety is conjugated to another compound which facilitates the colorimetric analysis, such as described herein.

In some aspects of the disclosure, the methods, compositions, or kits of include an oxidase or a peroxidase. As a general matter, an oxidase or a peroxidase can be used to generate a radical resulting in the transfer of electrons from one component to another. When the aromatic amine chromogenic substrate is present, it becomes oxidized to a chromogenic reaction product and the color of the reaction composition changes.

In some cases the oxidase or peroxidase is coupled to a binding moiety for the detection of an analyte. In these cases, the oxidase or peroxidase can simply serve to cause reduction of a peroxide compound, such as hydrogen peroxide, providing a chemical environment for the oxidation of the aromatic amine chromogenic substrate to a desired colored reaction product. Commercially available peroxidase conjugates, such as those described herein, can be used.

In other cases the oxidase or peroxidase has specificity towards an analyte of interest in the biological sample. For example, glucose oxidase (GOx) (EC 1.1.3.4) is an oxidoreductase that catalyses the oxidation of glucose to hydrogen peroxide and D-glucono-δ-lactone. In order to quantitate the amount of glucose in a biological sample, glucose oxidase and a peroxidase, such as horseradish peroxidase, can be added directly to the sample. Glucose oxidase, which causes the formation of hydrogen peroxide, can be reduced to provide conditions resulting in the oxidation of the aromatic amine chromogenic substrate. Xanthine oxidase is another enzyme that generates hydrogen peroxide by using hypoxanthine and xanthine as substrates. L-gulonolactone oxidase (EC 1.1.3.8) catalyzes the reaction of D-glucuronolactone to L-xylo-hex-3-gulonolactone and hydrogen peroxide. Using this type of approach, the analyte or the analyte binding member does not have be immobilized on a solid surface, such as performed using ELISA. Other oxidases include galactose oxidase, hexose oxidase, and pyranose oxidase.

Peroxidase enzymes useful for the methods of the disclosure can be obtained from a variety of sources, such as plants. Common, commercially available peroxidases are from horseradish and soybean. Horseradish peroxidase has an approximate molecular weight of 44 kDa, and is a single chain polypeptide glycoprotein with disulfide bridges that includes hemin plus $Ca^{2+}$. HRP specific activity can be expressed in pyrogallol units (one pyrogallol unit will form 1.0 mg purpurogallin from pyrogallol in 20 sec at pH 6.0 at 20° C.) or ABTS units (one ABTS unit will oxidize 1 μmole of ABTS per minute at 25° C. at pH 5.0). HRP can be inhibited by sodium azide, L-cystine, dichromate, ethylenethiourea, hydroxylamine, sulfide, p-aminobenzoic acid, $Cd^{+2}$, $Co^{+2}$, $Cu^{+2}$, $Fe^{+3}$, $Mn^{+2}$, $Ni^{+2}$, and $Pb^{+2}$.

Other peroxidases include lactoperoxidase, microperoxidase, NADH peroxidase NADPH peroxidase, fatty-acid peroxidase, and catalase.

In some modes of practice, a "peroxidase conjugate" is used in the methods for detecting an analyte. A conjugate generally refers to a compound that comprises two substances, wherein one of the substances is coupled to the other. Coupling of the conjugate can be covalent or non-covalent. A peroxidase conjugate can be one where a peroxidase enzyme is coupled to a binding moiety that detects the analyte, or that detects the binding moiety that detects the analyte. Exemplary peroxidase conjugates that can be commercially obtained include avidin-peroxidase conjugates, monoclonal anti-FLAG™ M2-peroxidase conjugates, anti-glutathione-S-transferase (GST)-peroxidase conjugates, anti-mouse IgG-peroxidase conjugates, anti-goat/sheep IgG-peroxidase conjugates, Protein G-peroxidase conjugates, Protein-A peroxidase conjugates, anti-rabbit IgG-peroxidase conjugates, and strepavidin-peroxidase conjugates, from, for example, Sigma-Aldrich.

A biological sample that includes an analyte can be placed in an analysis vessel, such as a well in a multiwall plate, so the analyte can be immobilized and then detected using methods of the disclosure. Typically, steps for the immobilization of the analyte or analyte binding member (e.g., antibody), binding of analyte binding member to the analyte, and subsequent binding of the analyte-analyte binding member complex can be performed using a suitable solutions, including incubation, blocking, and washing buffers. The solution can be an aqueous buffered solution, to maintain absorption of the analyte and/or analyte binding member on the plastic surface, and maintain protein configuration for proper binding and enzymatic activities. The blocking solution can include a non-specific protein such as bovine serum albumin, which can effectively block vessel binding sites that remain following initial coating steps in ELISA procedures (e.g. 5% BSA-PBS). Washing buffers can include a surfactant such as Tween (an exemplary washing buffer, PBS-T, contains 10 mM phosphate buffer pH 7.4, 150 mM NaCl, and 0.05% Tween 20).

In some modes of practice, an analysis vessel (such as a multi-well plate) is provided that has an amount of peroxidase immobilized on a solid surface of the vessel. Again, the peroxidase can be immobilized by its conjugation to a binding member, with the binding member directly or indirectly bound to an analyte previously immobilized on the vessel surface, using either an analyte binding member, or by the analyte being absorbed directly on the surface of the vessel. The amount of immobilized peroxidase can correlate with the amount of immobilized analyte, which correlates with the amount of analyte present in a sample. In control wells, standards with known amounts of analyte can be used.

In order to explain modes of practicing embodiments of the disclosure, in exemplary embodiments, analyte immobilization results in the corresponding immobilization of picogram quantities of a peroxidase enzyme, such as horseradish peroxidase, on a surface of a single well of a 96-well plate, such as an amount in the range of about 0.1 pg to about 100 ng (100,000 pg), about 1 pg to about 10 ng (10,000 pg), or about 1 pg to about 1 ng (1000 pg). In this case, the peroxidase enzyme is immobilized prior to adding the enzyme substrate, N,N,N-trimethylglycine solubilization reagent, and aromatic amine chromogenic substrate.

As a general matter, a peroxide substrate is added to the peroxidase, which is immobilized on a surface of the vessel, or present in solution in the vessel. A cost-effective substrate for carrying out peroxidase reactions is hydrogen peroxide. HRP combines with hydrogen peroxide ($H_2O_2$) and can carry out heterolytic cleavage of the $H_2O_2$ oxygen-oxygen bond. The complex can oxidize a wide variety of aromatic amine chromogenic substrates. The reaction can be monitored spectrophotometrically, and can optionally be stopped by the addition of a stop reagent compound such as one described herein.

Hydrogen peroxide, the N,N,N-trimethylglycine solubilization reagent, and the aromatic amine chromogenic substrate can be present in a reaction solution, which can be added to a reaction vessel that includes the peroxidase enzyme. The reaction solution can be prepared from components of a kit that include the N,N,N-trimethylglycine solubilization reagent, aromatic amine chromogenic substrate, hydrogen peroxide, and reaction buffer. In some embodiments the hydrogen peroxide, N,N,N-trimethylglycine solubilization reagent, and aromatic amine chromogenic substrate are supplied in a ready-to-use one component system. In other embodiments the N,N,N-trimethylglycine solubilization reagent, aromatic amine chromogenic substrate, and hydrogen peroxide are provided to a user separately, in a kit. For example, hydrogen peroxide can be provided as a concentrated stock solution (e.g., ~2-3%). The concentrated hydrogen peroxide can be diluted in the reaction solution to exemplary amounts in the range of about 0.1 mM to about 50 mM (~3×10$^{-4}$% to ~0.17%), or about 0.5 mM to about 10 mM (·0.0017% to ~0.034%). The kit can also include a reaction buffer, such as sodium phosphate (pH 7-8) provided in dry or concentrated form. For example, the buffer can be supplied as a 5× or 10× concentrate which can then be diluted in the reaction composition to a working concentration, such as in the range of about 10 mM to about 75 mM. The kit can also include an acid, such as citric acid, to adjust the pH of the reaction composition to one in the range of about 2.5 to about 4.5, or about 3 to about 4. In other embodiments the kit includes a composition wherein the acid is premixed with the N,N,N-trimethylglycine solubilization reagent and the aromatic amine chromogenic substrate.

The N,N,N-trimethylglycine solubilization reagent and aromatic amine chromogenic substrate can be reconstituted from dry form or diluted from a stock solution (individually or pre-mixed) and then added to the reaction solution. The kit can optionally include one or more liquids other than water or an aqueous reaction buffer for dissolving the materials. The working concentration of the chromogenic substrate can be chosen based on the type of chromogenic substrate, the amount of hydrogen peroxide, and/or the amount of analyte (and corresponding peroxidase) in the sample being analyzed. Exemplary ranges of the chromogenic substrate are from about 0.5 µM to about 10 mM, from about 10 µM to about 5 mM, or about 100 µM to about 3 mM, as described herein.

Optionally, a cosolvent can be included in the reaction composition with the analyte, enzyme, N,N,N-trimethylglycine solubilization reagent, and aromatic amine chromogenic substrate. The cosolvent can ensure the reagents of the reaction composition be maintained in soluble form and do not precipitate out of solution during the reaction, or later, such as upon addition of the stop reagent. Exemplary co-solvents include alcohols (i.e. methanol, ethanol, propanol), polyalcohols (i.e. glycerol, propylene glycol), dimethylsulfoxide, dimethylformamide, N-methylpyrrolidone (NMP), acetonitrile and similar solvents. Other solvents to improve solubility are well known in formulation art for in vitro diagnostic applications, and are included herein. A cosolvent can be used in the reaction composition at an exemplary concentration in the range of about 1% (v/v) to about 50% (v/v), or about 5% (v/v) to about 25% (v/v).

In some modes of practice, the reaction solution that includes the components sufficient for color development of the aromatic amine chromogenic substrate can then be added directly to the vessel that includes a peroxidase enzyme. Alternatively, components of the kit can be mixed directly in the wells. Using multiwall plates, the reaction solution can be dispensed, for example, by pipetting, in the well manually or using automated apparatus. Multi-tip pipetting apparatus can be used to increase the speed of the dispensing and or mixing process. Using a 96-well plate format, typical reaction volumes range from about 25 µL to about 200 µL, or from about 50 µL to about 150 µL.

The peroxidase reaction resulting in the conversion of the aromatic amine chromogenic substrate into the chromogenic product can be carried out for a desired period of time at a desired temperature. The reaction can be monitored visually or spectrophotometrically to determine the development of color in the composition. The incubation step will typically occur at room temperature, although a temperature in the range of about 10° C. to about 50° C. can be employed. Incubation times will typically range from about 1 to about 60 minutes, or more usually about 5 to about 45 minutes.

In order to describe aspects of the disclosure, 3,3',5,5'-tetramethylbenzidine (TMB) is used as the chromogenic substrate in the presence of an immobilized HRP enzyme (associated with the analyte), hydrogen peroxide, and N,N,N-trimethylglycine solubilization reagent. TMB, in the presence of HRP and $H_2O_2$ is oxidized to form a blue product ($\lambda_{max}$ 652), as previously described. The reaction can be observed visually, or the absorbance of the reaction can be monitored spectrophotometrically (e.g., at about 650 nm) to obtain an absorbance value corresponding to the blue color.

In some modes of practice, analysis of the reaction product is performed under "stopped" conditions. By this it is meant that the reaction is allowed to proceed for a predetermined period and then terminated with a stop reagent. As such, optionally, a stop reagent can be added when the reaction reaches a desired color, or when a certain absorbance value is reached. For example, in the case of TMB oxidation, or other chromogenic substrates that have similar absorbance properties upon oxidation, a stop reagent can be added to the reaction composition when the wells with the highest signals reach an absorbance of up to about 1.6 absorbance units at about 650 nm. Addition of the stop reagent converts the blue reaction product to a yellow product with an absorbance maxima at about 450 nm. The extinction coefficient of the yellow TMB product is about 2.3 times that of the blue TMB. Allowing the blue product to develop to about 1.5 or 1.6 absorbance at 650 nm results in an absorbance between 3.5 and 4 absorbance units upon the addition of stop reagent, which represents a practical high end for absorbance readings.

Exemplary stop reagents include acids such as sulfuric acid and hydrochloric acid, as well as sulfonic acid compounds as described in commonly assigned U.S. Publication No. 2013/0252261 (Sep. 26, 2013; Opperman et al.), such as methanesufonic acid (methylsulfonic acid; $CH_3SO_3H$), ethanesufonic acid (ethylsulfonic acid; $CH_3CH_2SO_3H$), propanesufonic acid, sulfamic acid (also known as amidosulfonic acid; $H_2NSO_3H$); aminomethanesulfonic acid, 2-aminoethanesulfonic acid (taurine), and aminoproanesulfonic acid. In an exemplary mode of practice, the stop reagent is 2× concentrated, or thereabouts, so the volume of stop reagent added to the well is approximately the same as the reaction volume in the well. For example, 100 µL of stop reagent is added to 100 µL of the reaction composition. Exemplary concentrations of stop reagent are in the range of about 1.5× to about 5×, which can be used to facilitate rapid mixing of the stop reagent and reaction components.

In some aspects a stop reagent is added to the reaction composition to provide a final concentration of stop reagent in the range of about 0.02 M to about 2.0 M, about 0.02 M to about 1 M, about 0.02 M to about 0.5 M, or about 0.02 to 0.2 M.

In methods using TMB as the aromatic amine chromogenic substrate, the color of the reaction composition can transition to yellow corresponding to the two-electron oxidation product of TMB ($\lambda_{max}$ 450). In some modes of practice, a stop reagent stabilizes the two-electron oxidation product, resulting in a yellow composition that maintains high levels of absorbance at about 450 nm when monitored spectrophotometrically.

In some methods of analyzing, such as using a direct or sandwich immunoassay as described herein, and the reagents employed, the absorbance of the chromogenic product as determined by a spectrophotometric method will be directly proportional to the amount of analyte in the sample. Where one is interested in a qualitative result or a semi-quantitative result, such as determining whether the amount of analyte is above a predetermined threshold, versus determining the concentration of analyte, the amount of peroxidase enzyme and/or chromogenic substrate can be selected to provide a clear signal as compared to the absence of analyte or analyte below the predetermined value.

In a kinetic analysis (e.g., kinetic ELISA), absorbance is continuously monitored. For example, a substrate is added to a microplate well, and the optical density increase over time is monitored continuously. In kinetic analysis, analyte concentrations are determined by slope of the reaction curve, rather than by the absolute optical density value reached (as compared to end-point ELISA). Slopes of the reaction curve are desirably determined before enzyme velocity begins to deviate from maximum. Data from kinetic analysis can be expressed as the change in milli-optical density units over time, or $\Delta mOD/\Delta t$. Using the initial absorbance reading of the mixture as its own blank, for example, the time ("reaction time") required for the absorbance to increase by a specific amount (e.g., greater or equal to 0.200 absorbance units), is determined. The reaction time for each sample of each product corresponds to the analyte concentration for that sample. The absolute value of analyte concentration for the sample is determined by comparison of the reaction time for the sample with the reaction time for at least one control solution whose analyte concentration is known. The ratio of reaction times for the unknown relative to the known sample is inversely proportional to the ratio of their concentrations.

For quantitation, absorbance can be accurately measured using appropriate hardware and software. Controls can be employed, where the signal to concentration of the analyte is determined, so that the signal can be directly related to the concentration of analyte in the immunoassay sample. In this manner, both the presence and the amount of analyte in the sample can be determined. Simple spectrophotometers, such as UV/Vis spectrophotometers for wavelengths between 175 nm and 900 nm capable of determining the absorbance of a sample are commercially available, for example, from Perkin Elmer. In analyzing the sample, a light of a specific wavelength, such as selected by an optical filter or monochromator, is transmitted through the sample, and a detector measures the percentage of the initial transmitted through the sample. The amount of transmitted light is generally inversely proportional to the amount of analyte in the sample. In other modes of practice, analysis is performed using a microplate reader. A variety of microplate readers are also commercially available that are capable of accommodating and analyzing the absorbance of samples in the wells of 96-well plates, are commercially available, from, for example BioTek (Winooski, Vt.).

Example 1

Betaine (N,N,N-trimethylglycine) was used as a non-encapsulating solubilization reagent to provide faster kinetics and increased dye content for a 3,3'5,5'-tetramethylbenzidine (TMB) substrate.

A TMB solution was prepared having the following concentration of reagents: 3 mM TMB (Sigma, Cat #T-2885), 0.5% dimethylsulfoxide (DMSO; Burdick and Jackson, Cat #081-4), 1.25 mM hydroxypropyl beta-cyclodextrin (Wacker, 60082620), 0.01% hydrogen peroxide (Sigma, Cat #H3410), and citric acid (Sigma, Cat #C1909) to pH 3.5.

Various chemicals, used at 0.5M in the TMB solution, were compared against the betaine reagent in non-encapsulation solubilization methods. Glycine (Sigma, Cat #G8898), sarcosine (Sigma, Cat #131776), choline chloride (Sigma, Cat #C1909), L-carnitine (Sigma, Cat #C0158), 3-(1-pyridinio)-1-propanesulfonate (Sigma, Cat #82804), or the betaine N,N,N-trimethylglycine (Sigma, Cat #B2629) were all added to separate scintillation vials of TMB solution.

A Nunc Maxisorb 96 microwell plate (Cat #439454) was coated with 100 μL of an 850 ng/mL solution of Rabbit Anti-Peroxidase (Accurate Chemical and Scientific Corporation, Cat #ACZ001021). The plate was then coated with 150 μL of StabilCoat (SurModics, Cat #SC01) for one hour. This was then aspirated and the plate was allowed to dry overnight in a desiccation chamber. Plates were then incubated with 100 μL of 3.125 ng/mL solution of HRP in Stabilzyme HRP Conjugate stabilizer (SurModics, SZ02) for one hour, washed three times, and 100 uL of TMB substrate was added to each well. The kinetics of the enzyme were monitored over a period of 15 minutes and the kinetic rate between 0-1 OD at A (650 nm) and 0-15 minutes was determined to provide mAU/min values.

Each TMB substrate and TMBW (available from SurModics, Inc) in an amount of 20 μL were added to individual aliquots of 980 μL of distilled water. These were measured in a quartz cuvette at A (285 nm) to determine the amount of unrestricted benzidine rings in solution. The results are shown in Table 1.

TABLE 1

|  | Dye ($A_{285}$) | Kinetics (mAu/min) |
| --- | --- | --- |
| Glycine | 0.358 | 41.16 |
| Sarcosine | 0.45 | 45.014 |
| Choline Chloride | 1.074 | 2.855 |
| DL-Carnitine | 0.254 | 18.432 |
| 3-(1-Pyridinio)-1-propanesulfonate | 1.175 | 49.732 |
| Betaine (N,N,N-trimethylglycine) | 0.974 | 71.917 |
| Base (Base No Additives) | 0.425 | 45.224 |
| TMBW | 0.445 | 55.386 |

Example 2

TMB solutions were prepared with the betaine N,N,N-trimethylglycine (Sigma, Cat #B2629) at variable concentrations (0.25M, 0.5M, and 1M), 0.5% DMSO (Burdick and Jackson, Cat #081-4), and 3 mM TMB (Sigma, Cat #T-2885) and pH adjusted to 3.5 with citric acid (Sigma, Cat #C1909) in distilled water.

Each TMB solution in an amount of 20 μL was added to individual aliquots of 980 μL of distilled water. These were measured in a quartz cuvette at A (285 nm) to determine the amount of unrestricted benzidine rings in solution. The results are shown in Table 2.

TABLE 2

| N,N,N-trimethylglycine Conc. | Dye ($A_{285}$) |
|---|---|
| 0.25M | 0.35 |
| 0.5M | 0.535 |
| 1M | 0.85 |

Example 3

TMB solutions were prepared using 3 mM TMB (Sigma, Cat #T-2885), 0.5% DMSO (Burdick and Jackson, Cat #081-4), 0.01% hydrogen peroxide (Sigma, Cat #H3410), and citric acid (Sigma Cat #C1909) to pH 3.5. To each TMB solution was added 1 mM hydroxy propyl beta-cyclodextrin (Wacker, 60082620), 3 mm hydroxy propyl beta-cyclodextrin (Wacker, 60082620), or 0.5M of the betaine N,N,N-trimethylglycine (Sigma, Cat #B2629).

A Nunc Maxisorb 96 microwell plate (Cat #439454) was coated with 100 μL of an 850 ng/mL solution of Rabbit Anti-Peroxidase (Accurate Chemical and Scientific Corporation, Cat #ACZ001021). The plate was then coated with 150 μL of StabilCoat (SurModics, Cat #SC01) for one hour. This was then aspirated and the plate was allowed to dry overnight in a desiccation chamber. Plates were then incubated with 100 μL of 3.125 ng/mL solution of HRP in Stabilzyme HRP Conjugate stabilizer (SurModics, SZ02) for one hour, washed three times, and 100 uL of TMB substrate was added to each well. The kinetics of the enzyme were monitored over a period of 15 minutes and the kinetic rate between 0-1 OD at A (650 nm) and 0-15 minutes was determined to provide mAU/min values.

Each TMB substrate and TMBW (available from Sur-Modics, Inc) in an amount of 20 μL of were added to individual aliquots of 980 μL of distilled water. These were measured in a quartz cuvette at A (285 nm) to determine the amount of unrestricted benzidine rings in solution. The results are shown in Table 3.

TABLE 3

| Sample | pH | Dye ($A_{285}$) | Kinetics (mAu/min) |
|---|---|---|---|
| Control (Base No Additives) | 3.54 | 0.288 | 41.86 |
| 1 mM Beta Cyclodextrin | 3.51 | 0.339 | 39.697 |
| 3 mM Beta Cyclodextrin | 3.52 | 0.78 | 49.775 |
| 0.5M Betaine | 3.55 | 1.061 | 71.739 |
| TMBW | 3.55 | 0.465 | 49.037 |

What is claimed is:

1. An aqueous composition for colorimetric analysis comprising a benzidine chromogenic substrate and N,N,N-trimethylglycine, wherein the benzidine chromogenic substrate is 3,3',5,5' tetramethylbenzidine (3,3',5,5' TMB) wherein the N,N,N-trimethylglycine is present in the composition in the range of 0.25 M to 1 M, wherein the composition has a pH in the range of 3 to 4, wherein the N,N,N-trimethylglycine and 3,3',5,5' TMB are present in the composition in a molar ratio in the range of 20:1 to 1,000:1, and wherein the N,N,N-trimethylglycine improves the solubility of the 3,3',5,5' TMB in the aqueous composition.

2. The composition of claim 1, wherein the N,N,N-trimethylglycine is present in the composition in the range of 0.5 M to 1 M.

3. The composition of claim 1 further comprising a peroxidase, an oxidase, or a conjugate of a peroxidase or an oxidase with an analyte-specific binding moiety.

4. The composition of claim 3 wherein the peroxidase and/or oxidase is selected from the group consisting of horseradish peroxidase, soybean peroxidase, glucose oxidase, galactose oxidase, xanthine oxidase, lactoperoxidase, microperoxidase, NADH peroxidase NADPH peroxidase, fatty-acid peroxidase, and catalase.

5. The composition of claim 4 wherein the peroxidase is a derivative of horseradish peroxidase (HRP).

6. A kit for colorimetric analysis comprising the composition of claim 1, and one or more of the following: (a) an analysis plate upon which a colorimetric analysis can be performed; (b) an analyte specific binding member; (c) an analyte positive control; or (d) an analyte negative control.

* * * * *